(12) United States Patent
Essaddam et al.

(10) Patent No.: US 12,415,901 B2
(45) Date of Patent: *Sep. 16, 2025

(54) PROCESS FOR THE DEPOLYMERIZATION OF POLYETHYLENE TEREPHTHALATE (PET)

(71) Applicant: 9449710 CANADA INC., Terrebonne (CA)

(72) Inventors: Adel Essaddam, Terrebonne (CA); Fares Essaddam, Terrebonne (CA)

(73) Assignee: 9449710 CANADA INC., Terrebonne (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/461,443

(22) Filed: Sep. 5, 2023

(65) Prior Publication Data

US 2024/0309170 A1    Sep. 19, 2024

Related U.S. Application Data

(63) Continuation of application No. 17/529,643, filed on Nov. 18, 2021, now Pat. No. 11,795,291, which is a continuation of application No. 16/821,870, filed on Mar. 17, 2020, now Pat. No. 11,248,103.

(60) Provisional application No. 62/821,270, filed on Mar. 20, 2019.

(51) Int. Cl.
*C08J 11/24*    (2006.01)

(52) U.S. Cl.
CPC ............ *C08J 11/24* (2013.01); *C08J 2367/02* (2013.01)

(58) Field of Classification Search
USPC ...................................................... 528/48.5
See application file for complete search history.

(56) References Cited

U.S. PATENT DOCUMENTS

| | | | |
|---|---|---|---|
| 2,884,443 A | 4/1959 | Erhard et al. | |
| 3,219,622 A | 11/1965 | Luciano et al. | |
| 3,321,510 A | 5/1967 | Rudolf et al. | |
| 3,403,115 A | 9/1968 | Hans et al. | |
| 3,501,420 A | 3/1970 | Stevenson et al. | |
| 3,520,940 A | 7/1970 | Smith, Jr. et al. | |
| 3,776,945 A | 12/1973 | Ligorati et al. | |
| 4,163,860 A | 8/1979 | Delattre et al. | |
| 4,230,892 A | 10/1980 | Pruckmayr | |
| 4,263,413 A | 4/1981 | Gardner et al. | |
| 4,355,175 A | 10/1982 | Pusztaszeri | |
| 4,525,307 A | 6/1985 | Pratt | |
| 4,584,414 A | 4/1986 | Pruckmayr | |
| 5,045,122 A | 9/1991 | Tindall et al. | |
| 5,051,528 A | 9/1991 | Naujokas et al. | |
| 5,236,959 A * | 8/1993 | Oakley | C08J 11/24 524/34 |
| 5,328,982 A | 7/1994 | Tindall et al. | |
| 5,386,055 A | 1/1995 | Lee et al. | |
| 5,668,186 A | 9/1997 | Brunelle et al. | |
| 5,952,520 A | 9/1999 | Naujokas | |
| 6,528,546 B2 | 3/2003 | Lee et al. | |
| 6,670,503 B2 | 12/2003 | Broccatelli | |
| 6,706,843 B1 | 3/2004 | Ishihara et al. | |
| 6,720,448 B2 | 4/2004 | Broccatelli | |
| 6,911,546 B2 | 6/2005 | Hedrick et al. | |
| 6,916,936 B2 | 7/2005 | Hedrick et al. | |
| 7,053,221 B2 | 5/2006 | Hedrick et al. | |
| 7,462,649 B2 | 12/2008 | Nakao et al. | |
| 7,544,800 B2 | 6/2009 | Hedrick et al. | |
| 7,750,057 B2 | 7/2010 | Ogasawara | |
| 7,893,122 B2 | 2/2011 | Fregoso-Infante et al. | |
| 8,309,618 B2 | 11/2012 | Hedrick et al. | |
| 8,492,504 B2 | 7/2013 | Hedrick et al. | |
| 8,513,379 B2 | 8/2013 | Matsumura | |
| 9,550,713 B1 | 1/2017 | Essaddam | |
| 10,087,130 B2 | 10/2018 | Essaddam | |
| 10,251,976 B2 | 4/2019 | Erbe et al. | |
| 10,252,976 B1 | 4/2019 | Essaddam et al. | |
| 10,640,442 B2 | 5/2020 | Essaddam | |
| 10,793,508 B2 | 10/2020 | Essaddam et al. | |
| 10,808,096 B2 | 10/2020 | Essaddam et al. | |
| 11,248,103 B2 * | 2/2022 | Essaddam ............... C07C 67/03 |
| 11,401,398 B2 | 8/2022 | Essaddam et al. | |
| 11,554,366 B2 | 1/2023 | Essaddam et al. | |
| 11,795,291 B2 * | 10/2023 | Essaddam ........... C07C 29/1285 |
| 11,866,404 B2 | 1/2024 | Essaddam et al. | |
| 2005/0027023 A1 | 2/2005 | Masuda et al. | |
| 2008/0242751 A1 | 10/2008 | Kurian et al. | |
| 2009/0032015 A1 | 2/2009 | Myllymaki et al. | |

(Continued)

FOREIGN PATENT DOCUMENTS

| | | |
|---|---|---|
| CA | 2069500 A1 | 6/1991 |
| CN | 1585798 A | 2/2005 |

(Continued)

OTHER PUBLICATIONS

EA202490294 Eurasian Search Report dated Aug. 20, 2024.
Karayannidis, G. P. et al. Poly(ethylene terephthalate) Recycling and Recovery of Pure Terephthalic Acid by Alkaline Hydrolysis. Advances in Polymer Technology 21(4):250-259 (2002).
Shen, Guo-liang et al. Study on synthesis technology of ethylene glycol sodium by sodium hydroxide method. Chemical Engineer 9:5-6 (2010). (English abstract).
ACS. Common Organic Solvents: Table of Properties. downloaded from https://www.organicdivision.org/orig/organic_solvents.html on Apr. 4, 2018, p. 1-2).
Adeakin et al. Polymer—Solvent Relation: Swelling and Fibre Morphology. IOSR-JPTE 4(2):27-28 (2017).

(Continued)

*Primary Examiner* — Terressa Boykin
(74) *Attorney, Agent, or Firm* — WILSON SONSINI GOODRICH & ROSATI

(57) ABSTRACT

The present disclosure relates to the formation of dimethyl terephthalate (DMT) and mono ethylene glycol (MEG). The present invention also relates to the depolymerization of polyethylene terephthalate (PET) and the recovery of dimethyl terephthalate (DMT) and mono ethylene glycol (MEG) using sodium methoxide as a catalyst.

20 Claims, No Drawings

(56) References Cited

U.S. PATENT DOCUMENTS

| | | | |
|---|---|---|---|
| 2009/0171113 | A1 | 7/2009 | Anderson et al. |
| 2009/0318579 | A1 | 12/2009 | Ikenaga |
| 2011/0004014 | A1 | 1/2011 | Hedrick et al. |
| 2013/0345453 | A1 | 12/2013 | Sipos et al. |
| 2015/0315325 | A1 | 11/2015 | Tabor et al. |
| 2016/0237243 | A1 | 8/2016 | Woldt et al. |
| 2017/0008826 | A1 | 1/2017 | Essaddam |
| 2017/0113995 | A1 | 4/2017 | Mastrangelo |
| 2018/0370984 | A1 | 12/2018 | Morvan et al. |
| 2019/0084916 | A1 | 3/2019 | Essaddam et al. |
| 2019/0290035 | A1 | 9/2019 | Nieraad et al. |
| 2019/0390035 | A1 | 12/2019 | Essaddam et al. |
| 2020/0157307 | A1 | 5/2020 | Guo |
| 2020/0392067 | A1 | 12/2020 | Essaddam et al. |
| 2021/0030960 | A1 | 2/2021 | Huang et al. |
| 2023/0125080 | A1 | 4/2023 | Essaddam et al. |
| 2023/0374249 | A1 | 11/2023 | Essaddam et al. |

FOREIGN PATENT DOCUMENTS

| | | | |
|---|---|---|---|
| CN | 101628909 | A | 1/2010 |
| CN | 102746460 | A | 10/2012 |
| CN | 104327254 | A | 2/2015 |
| CN | 105601507 | A | 5/2016 |
| CN | 104327254 | B | 6/2016 |
| CN | 108047023 | A | 5/2018 |
| DE | 513677 | C | 12/1930 |
| EP | 1710226 | A1 | 10/2006 |
| FR | 1081681 | A | 12/1954 |
| FR | 2335490 | A1 | 7/1977 |
| GB | 729803 | A | 5/1955 |
| GB | 784248 | A | 10/1957 |
| GB | 787554 | A | 12/1957 |
| GB | 901094 | A | 7/1962 |
| GB | 1043671 | A | 9/1966 |
| GB | 2041916 | A | 9/1980 |
| JP | 48008745 | A | 2/1973 |
| JP | 50029459 | B | 9/1975 |
| JP | S61286351 | A | 12/1986 |
| JP | H0488745 | A | 3/1992 |
| JP | H051142 | A | 1/1993 |
| JP | 2000072720 | A | 3/2000 |
| JP | 2001192492 | A | 7/2001 |
| JP | 2001261707 | A | 9/2001 |
| JP | 2003055300 | A | 2/2003 |
| JP | 2006045371 | A | 2/2006 |
| JP | 2006052173 | A | 2/2006 |
| JP | 2008063305 | A | 3/2008 |
| JP | 4365592 | B2 | 11/2009 |
| JP | 4575074 | B2 | 11/2010 |
| JP | 2012116779 | A | 6/2012 |
| JP | 2012131729 | A | 7/2012 |
| JP | 2014070132 | A | 4/2014 |
| KR | 20180092147 | A | 8/2018 |
| WO | WO-9527753 | A1 | 10/1995 |
| WO | WO-9724310 | A1 | 7/1997 |
| WO | WO-9746611 | A1 | 12/1997 |
| WO | WO-9803459 | A1 | 1/1998 |
| WO | WO-0047659 | A1 | 8/2000 |
| WO | WO-0158982 | A1 | 8/2001 |
| WO | WO-0218471 | A2 | 3/2002 |
| WO | WO-0238276 | A1 | 5/2002 |
| WO | WO-2005003217 | A1 | 1/2005 |
| WO | WO-2006021063 | A1 | 3/2006 |
| WO | WO-2007076384 | A2 | 7/2007 |
| WO | WO-2007096326 | A1 | 8/2007 |
| WO | WO-2007113872 | A1 | 10/2007 |
| WO | WO-2007148353 | A1 | 12/2007 |
| WO | WO-2008007384 | A1 | 1/2008 |
| WO | WO-2017007965 | A1 | 1/2017 |
| WO | WO-2019051597 | A1 | 3/2019 |
| WO | WO-2020002999 | A2 | 1/2020 |
| WO | WO-2020188359 | A1 | 9/2020 |

OTHER PUBLICATIONS

Al-Sabagh et al. Greener routes for recycling of polyethylene terephthalate. Egyptian Journal of Petroleum 25(1):53-64 (2016).
Bae et al., The Characteristics of PET Micro Fiber Fabrics Decomposed dy Sodium Ethylene glycol Solution. Journal of the Korean Home Economics Association 36(8):95-104 (1998) (English Abstract).
Balcerzyk. Behavior of swollen poly(ethylene terephthalate) on the action of alkali solutions. Kolloid-Z.u.Z. Polymere 251:776-778 (1973).
Cho et al. Hydrophilic treatment of PET [poly(ethylene terephthalate)] fabric with monosodium ethylene glycolate. Journal of the Korean Fiber Society 23(2):80-87 (1986) (English Abstract).
Cho et al. Study on Decomposition Reactions of Poly(ethylene terephthalate) Films Treated with Mono-sodium Ethylene Glycolate. Journal of the Korean Society of Dyers and Finishers 2(3):26-35 (1990) (English Abstract).
Co-pending U.S. Appl. No. 18/538,336, inventors Essaddam; Adel et al., filed Dec. 13, 2023.
Falbe. Alcohols, Aliphatic—Ullmann's Encyclopedia of Industrial Chemistry. Downloaded from https://doi.org/10.1002/14356007.a01_279.pub2, first published Jan. 15, 2013, p. 1-26.
Feghali et al. Room Temperature Organocatalyzed Reductive Depolymerization of Waste Polyethers Polyesters and Polycarbonates. ChemSusChem. 8(6):980-984 (2015).
Haga. Anomalous Swelling of Poly(ethylene terephthalate) fiber in organic solvents. Journal of Polymer Science, Polymer Letters Edition 20:629-634 (1982).
Haga. Case II swelling of poly(ethylene terephthalate) in organic solvents. Journal of Applied Polymer Science 26(8):2649-2655 (1981).
Ishalina, O.V., Lakeev, S.N., Minnigulov, R.Z., & Majdanova, I.O. (2015). Analysis of polyethylene terephthalate waste recycling methods. Production and use of elastomers, (3), 39-48 (in Russian). https://cyberleninka.ru/article/n/analiz-metodov-pererabotki-othodov-polietilentereftalata.
Kouzu et al. Heterogeneous catalysis of calcium oxide used for transesterification of soybean oil with refluxing methanol. Applied Catalysis A: General 355:94-99 (2009).
Kurokawa et al. Methanolysis of polyethylene terephthalate (PET) in the presence of aluminium tiisopropoxide catalyst to form dimethyl terephthalate and ethylene glycol. Polymer Degradation and Stability 79(3):529-533 (2003).
Liu et al. Calcium methoxide as a solid base catalyst for the transesterification of soybean oil to biodiesel with methanol. Fuel 87:1076-1082 (2008).
Mishra et al. Kinetic and thermodynamic study of methanolysis of poly(ethylene terephthalate) waste powder. Polym Int 52:337-342 (2003).
Mohsin et al. Sodium Methoxide Catalyzed Depolymerization of Waste Polyethylene Terephthalate Under Microwave Irradiation. Catalysis in Industry 10:41-48 (2018).
Mohsin et al. Sodium Methoxide Catalyzed Depolymerization of Waste Polyethylene Terephthalate under Microwave Irradiation. Kataliz V Promyshlennosti 17(4):278-286 (2017).
Namboori et al. Steric effects in the basic hydrolysis of poly(ethylene terephthalate). Journal of Applied Polymer Science 12:1999-2005 (1968).
PCT/CA2018/051135 International Search Report and Written Opinion dated Dec. 4, 2018.
PCT/IB2019/000816 International Search Report and Written Opinion dated Jan. 3, 2020.
PCT/IB2020/000216 International Search Report and Written Opinion dated Jun. 25, 2020.
PCT/US2016/041392 International Search Report and Written Opinion dated Nov. 10, 2016.
Ramsden et al. Factors Influencing the Kinetics of the Alkaline Depolymerisation of Poly(ethylene terephthalate) I: The Effect of Solvent. J Chem Tech Biotechnol 67:131-136 (1996).
Sheehan. Terephthalic Acid, Dimethyl Terephthalate, and Isophthalic Acid. Ullmann's Encyclopedia of Industrial Chemistry 36:17-28 (2011).

(56) References Cited

OTHER PUBLICATIONS

Shukla et al. Glycolysis of polyethylene terephthalate waste fibers. Journal of Applied Polymer Science 98:513-517 (2005).
Sullivan et al. Mixed plastics waste valorization through tandem chemical oxidation and biological funneling. Science 378(6616):207-211 (2022).
U.S. Appl. No. 14/795,116 Office Action dated Jun. 2, 2016.
U.S. Appl. No. 15/377,460 Office Action dated Jan. 29, 2018.
U.S. Appl. No. 15/706,484 Office Action dated Apr. 13, 2018.
U.S. Appl. No. 15/706,484 Office Action dated Oct. 15, 2018.
U.S. Appl. No. 16/117,672 Office Action dated May 15, 2019.
U.S. Appl. No. 16/259,980 Office Action dated Feb. 4, 2020.
U.S. Appl. No. 16/450,807 Office Action dated Feb. 20, 2020.
U.S. Appl. No. 17/024,159 Office Action dated Dec. 1, 2021.
U.S. Appl. No. 17/024,159 Office Action dated Jul. 7, 2021.
U.S. Appl. No. 17/350,979 Office Action dated Aug. 10, 2022.
U.S. Appl. No. 17/350,979 Office Action dated Jan. 25, 2022.
U.S. Appl. No. 17/350,979 Office Action dated May 10, 2023.
U.S. Appl. No. 17/350,979 Office Action dated Nov. 22, 2022.
U.S. Appl. No. 17/350,979 Office Action dated Oct. 21, 2021.
U.S. Appl. No. 17/837,801 Notice of Allowance dated Apr. 10, 2024.
U.S. Appl. No. 17/837,801 Office Action dated Dec. 21, 2023.
U.S. Appl. No. 17/837,801 Office Action dated Jun. 23, 2023.
U.S. Appl. No. 18/228,531 Notice of Allowance dated Apr. 18, 2024.
U.S. Appl. No. 18/228,531 Office Action dated Jan. 4, 2024.
U.S. Appl. No. 18/228,531 Office Action dated Sep. 20, 2023.
U.S. Appl. No. 16/821,870 Office Action dated Jul. 26, 2021.
U.S. Appl. No. 17/529,643 Office Action dated Nov. 23, 2022.
Venkatachalam et al. Materials Science "Polyester"—Chapter 4: Degradation and Recyclability of Poly(Ehtylene Terephthalate). Intech 24 pgs. (2012).
Yan. Recycling plastic using a hybrid process. Science 378(6616):132-133 (2022).

* cited by examiner

PROCESS FOR THE DEPOLYMERIZATION OF POLYETHYLENE TEREPHTHALATE (PET)

CROSS-REFERENCE

This application is a continuation of U.S. application Ser. No. 17/529,643, filed on Nov. 18, 2021, which is a continuation of U.S. application Ser. No. 16/821,870, filed on Mar. 17, 2020, now U.S. Pat. No. 11,248,103, issued Feb. 15, 2022, which claims the benefit of U.S. Provisional Application Ser. No. 62/821,270 filed Mar. 20, 2019, each of which are incorporated herein by reference in their entirety.

FIELD OF THE INVENTION

The present disclosure relates to the formation of dimethyl terephthalate (DMT) and mono ethylene glycol (MEG) from polyethylene terephthalate (PET).

BACKGROUND OF THE INVENTION

The polyethylene terephthalate (PET) bottle resin market has been growing strongly as PET resins have replaced glass in carbonated soft drink, bottled water and food containers.

Dimethyl terephthalate (DMT) is primarily used in the manufacture of polyethylene terephthalate (PET) for fiber, film, container plastics, and specialty plastics applications.

The largest polyester sector is the fibers market where it is used to make clothes, home textiles, such as sheets and curtains, carpets and rugs, and industrial products, such as tire cord, seat belts, hoses and ropes. PET film is utilized in electrical applications, such as dielectric metal foil capacitors, and for food packaging.

SUMMARY OF THE INVENTION

Disclosed herein is a process for the depolymerization of polyethylene terephthalate (PET) comprised in a feedstock to form dimethyl terephthalate (DMT) and mono ethylene glycol (MEG); the process comprising:
(i) mixing the feedstock comprising polyethylene terephthalate (PET) with a first portion of methanol to form a first mixture;
(ii) adding sodium methoxide to the first mixture:
(iii) admixing: and
(iv) adding a second portion of methanol thereby forming a second mixture:
thereby forming dimethyl terephthalate (DMT) and mono ethylene glycol (MEG).

In some embodiments of a process for the depolymerization of polyethylene terephthalate (PET), the amount of the first portion of methanol is between about 0.1 and about 0.5 kg/kg of feedstock.

In some embodiments of a process for the depolymerization of polyethylene terephthalate (PET), the amount of the first portion of methanol is about 0.3 kg/kg of feedstock.

In some embodiments of a process for the depolymerization of polyethylene terephthalate (PET), step (i) is conducted for about 15 mins to about 120 mins.

In some embodiments of a process for the depolymerization of polyethylene terephthalate (PET), step (i) is conducted for about 60 min.

In some embodiments of a process for the depolymerization of polyethylene terephthalate (PET), step (i) is conducted at a temperature between about 50° C. to about 100° C.

In some embodiments of a process for the depolymerization of polyethylene terephthalate (PET), step (i) is conducted at a temperature between about 60° C. to about 90° C.

In some embodiments of a process for the depolymerization of polyethylene terephthalate (PET), step (i) is conducted at a temperature of about 60° C.

In some embodiments of a process for the depolymerization of polyethylene terephthalate (PET), step (i) is conducted at a temperature of about 80° C.

In some embodiments of a process for the depolymerization of polyethylene terephthalate (PET), step (iii) is conducted for about 10 min to about 120 min.

In some embodiments of a process for the depolymerization of polyethylene terephthalate (PET), step (iii) is conducted for about 30 min.

In some embodiments of a process for the depolymerization of polyethylene terephthalate (PET), step (iii) is conducted at a temperature between about 40° C. to about 100° C.

In some embodiments of a process for the depolymerization of polyethylene terephthalate (PET), step (iii) is conducted at a temperature of between about 85° C. to about 90° C.

In some embodiments of a process for the depolymerization of polyethylene terephthalate (PET), the second portion of methanol is provided to maintain the sodium methoxide concentration in the second mixture between about 0.2 wt-% and about 5.0 wt-%.

In some embodiments of a process for the depolymerization of polyethylene terephthalate (PET), the second portion of methanol is provided to maintain the sodium methoxide concentration in the second mixture between about 0.5 wt-% and about 1.5 wt-%.

In some embodiments of a process for the depolymerization of polyethylene terephthalate (PET), the second portion of methanol is provided to maintain the sodium methoxide concentration in the second mixture at about 0.7 wt-%.

In some embodiments of a process for the depolymerization of polyethylene terephthalate (PET), the second portion of methanol is provided in fractions at predetermined times.

In some embodiments of a process for the depolymerization of polyethylene terephthalate (PET), a first fraction of the second portion of methanol is provided about 1 min to about 60 min after the addition of sodium methoxide.

In some embodiments of a process for the depolymerization of polyethylene terephthalate (PET), a first fraction of the second portion of methanol is provided about 30 min after the addition of sodium methoxide.

In some embodiments of a process for the depolymerization of polyethylene terephthalate (PET), the amount of the first fraction of the second portion of methanol is between about 50 g/kg of feedstock and about 100 g/kg of feedstock.

In some embodiments of a process for the depolymerization of polyethylene terephthalate (PET), a second fraction of the second portion of methanol is provided about 30 min to about 90 min after the addition of sodium methoxide.

In some embodiments of a process for the depolymerization of polyethylene terephthalate (PET), a second fraction of the second portion of methanol is provided about 60 min after the addition of sodium methoxide.

In some embodiments of a process for the depolymerization of polyethylene terephthalate (PET), the amount of the second fraction of the second portion of methanol is between about 100 g/kg of feedstock and about 200 g/kg of feedstock.

In some embodiments of a process for the depolymerization of polyethylene terephthalate (PET), a third fraction of the second portion of methanol is provided about 60 min to about 120 min after the addition of sodium methoxide.

In some embodiments of a process for the depolymerization of polyethylene terephthalate (PET), a third fraction of the second portion of methanol is provided about 90 min after the addition of sodium methoxide.

In some embodiments of a process for the depolymerization of polyethylene terephthalate (PET), the amount of the third fraction of the second portion of methanol is between about 100 g/kg of feedstock and about 200 g/kg of feedstock.

In some embodiments of a process for the depolymerization of polyethylene terephthalate (PET), the second portion of methanol is provided continuously.

In some embodiments of a process for the depolymerization of polyethylene terephthalate (PET), the second portion of methanol is provided continuously at a rate between about 50 g/h/kg of feedstock and about 100 g/h/kg of feedstock.

In some embodiments of a process for the depolymerization of polyethylene terephthalate (PET), the ratio of sodium methoxide to polyethylene terephthalate (PET) is between about 1:2 and about 1:28 (mol/mol).

In some embodiments of a process for the depolymerization of polyethylene terephthalate (PET), the ratio of sodium methoxide to polyethylene terephthalate (PET) is between about 1:5 and about 1:20 (mol/mol).

In some embodiments of a process for the depolymerization of polyethylene terephthalate (PET), the ratio of sodium methoxide to polyethylene terephthalate (PET) is between about 1:10 and about 1:20 (mol/mol).

In some embodiments of a process for the depolymerization of polyethylene terephthalate (PET), the ratio of sodium methoxide to polyethylene terephthalate (PET) is between about 1:10 and about 1:15 (mol/mol).

In some embodiments of a process for the depolymerization of polyethylene terephthalate (PET), the dimethyl terephthalate is obtained in at least about 90 mol % yield.

In some embodiments of a process for the depolymerization of polyethylene terephthalate (PET), the dimethyl terephthalate is obtained in at least about 95 mol % yield.

In the dimethyl terephthalate is obtained in at least about 99 mol % yield.

In some embodiments of a process for the depolymerization of polyethylene terephthalate (PET), the mono ethylene glycol is obtained in at least about 80 mol % yield.

In some embodiments of a process for the depolymerization of polyethylene terephthalate (PET), the mono ethylene glycol is obtained in at least about 85 mol % yield.

In some embodiments of a process for the depolymerization of polyethylene terephthalate (PET), the mono ethylene glycol is obtained in at least about 90 mol % yield.

In some embodiments of a process for the depolymerization of polyethylene terephthalate (PET), the feedstock comprising polyethylene terephthalate (PET) is provided in the form of particles.

In some embodiments of a process for the depolymerization of polyethylene terephthalate (PET), the average particle size is between about 0.1 mm and about 20 mm.

In some embodiments of a process for the depolymerization of polyethylene terephthalate (PET), the average particle size is between about 5 mm and about 10 mm.

In some embodiments of a process for the depolymerization of polyethylene terephthalate (PET), the average particle size is up to about 6 mm.

In some embodiments of a process for the depolymerization of polyethylene terephthalate (PET), the average particle size is up to about 8 mm.

DETAILED DESCRIPTION OF THE INVENTION

Dimethyl terephthalate (DMT) is used in the production of polyesters. including polyethylene terephthalate (PET), polytrimethylene terephthalate (PTT), and poly butylene terephthalate (PBT). Because DMT is volatile, it is an intermediate in some schemes for the recycling of PET, e.g. from plastic bottles. Hydrogenation of DMT affords the diol 1,4-cyclohexanedimethanol, which is a useful monomer in the formation of polyester resins.

DMT has been produced in a number of ways. Conventionally, and still of commercial value, is the direct esterification of terephthalic acid. Alternatively, it is prepared by alternating oxidation and methyl-esterification steps from para-xylene via methyl para-toluate. The method for the production of DMT from para-xylene and methanol consists of four major steps: oxidation, esterification, distillation, and crystallization. A mixture of para-xylene and para-toluic ester is oxidized with air in the presence of a transition metal catalyst (Co/Mn). The acid mixture resulting from the oxidation is esterified with methanol to produce a mixture of esters. The crude ester mixture is distilled to remove all the heavy boilers and residue produced; the lighter esters are recycled to the oxidation section. The raw DMT is then crystallized to remove DMT isomers, residual acids, and aromatic aldehydes.

An improvement in DMT and MEG production from PET recycling: due to the growing use of PET in the packaging and fiber (carpet and other textile) industries there is a need for an efficient, low energy, high yielding, and cost effective way to form DMT and MEG from PET.

Feedstock

Described herein is a process for the depolymerization of polyethylene terephthalate (PET) comprised in a feedstock to form dimethyl terephthalate (DMT) and mono ethylene glycol (MEG).

In some embodiments, the feedstock comprising polyethylene terephthalate also comprises contaminants, such as additional polymers (for example polyethylene, polypropylene. polyvinyl chloride (PVC), polycarbonate (PC), polyvinylidene chloride (PVDC), and polyamides), paper, colorants, dirt, ethylene vinyl alcohol (EVOH), ethylene vinyl acetate (EVA), cellulose, glue, or any combination thereof. In some embodiments, the feedstock comprises between about 5% and about 30% contaminants.

Mishra et al. (Kinetic and thermodynamic study of methanolysis of poly (ethylene terephthalate) waste powder Polym. Int. 52:337-342 (2003)) have shown that an increase in the particle size of PET flakes causes a decrease in depolymerization. Mishra et al. recorded 127.5 µm as the optimal particle size. There is a need for a depolymerization process that allows for the use of bigger feedstock particles. In some embodiments, the feedstock comprising polyethylene terephthalate (PET) is provided in the form of particles. In some embodiments, the average particle size is between about 0.1 mm and about 20 mm. In some embodiments, the average particle size is between about 5 mm and about 10 mm. In some embodiments, the average particle size is up to about 5 mm. In some embodiments, the average particle size is up to about 6 mm. In some embodiments, the average particle size is up to about 7 mm. In some embodiments, the average particle size is up to about 8 mm. In some embodiments, the average particle size is up to about 9 mm. In some embodiments, the average particle size is up to about 10 mm. In some embodiments, the average particle size is up to about 11 mm. In some embodiments, the average particle size is up to about 12 mm. In some embodiments, the average particle size is up to about 13 mm. In some embodiments, the average particle size is up to about 14 mm. In some embodiments, the average particle size is up to about 15 mm. In some embodiments, the average particle size is up to about 16 mm. In some embodiments, the average particle size is up to about 17 mm. In some embodiments, the average particle size is up to about 18 mm. In some embodiments, the average particle size is up to about 19 mm. In some embodiments, the average particle size is up to about 20 mm.

DMT

Described herein is a process for the depolymerization of polyethylene terephthalate (PET) comprised in a feedstock to form dimethyl terephthalate (DMT) and mono ethylene glycol (MEG).

In some embodiments, the DMT contains less than about 10% impurity (w/w). In some embodiments, the DMT contains less than about 9% impurity (w/w). In some embodiments. the DMT contains less than about 8% impurity (w/w). In some embodiments, the DMT contains less than about 7% impurity (w/w). In some embodiments, the DMT contains less than about 6% impurity (w/w). In some embodiments, the DMT contains less than about 5% impurity (w/w). In some embodiments, the DMT contains less than about 4% impurity (w/w). In some embodiments, the DMT contains less than about 3% impurity (w/w). In some embodiments, the DMT contains less than about 2% impurity (w/w). In some embodiments, the DMT contains less than about 1% impurity (w/w). In some embodiments, the DMT contains less than about 0.5% impurity (w/w). In some embodiments, the DMT contains less than about 0.4% impurity (w/w). In some embodiments, the DMT contains less than about 0.3% impurity (w/w). In some embodiments, the DMT contains less than about 0.2% impurity (w/w). In some embodiments, the DMT contains less than about 0.1% impurity (w/w).

In some embodiments, the DMT contains less than about 250 ppm of any metals, less than about 240 ppm of any metals, less than about 230 ppm of any metals, less than about 220 ppm of any metals, less than about 210 ppm of any metals, less than about 200 ppm of any metals, less than about 190 ppm of any metals, less than about 180 ppm of any metals, less than about 170 ppm of any metals, less than about 160 ppm of any metals, less than about 150 ppm of any metals, less than about 140 ppm of any metals, less than about 130 ppm of any metals, less than about 120 ppm of any metals, less than about 110 ppm of any metals, less than about 100 ppm of any metals, less than about 90 ppm of any metals, less than about 80 ppm of any metals, less than about 70 ppm of any metals, less than about 60 ppm of any metals, less than about 50 ppm of any metals, less than about 40 ppm of any metals, less than about 30 ppm of any metals, less than about 20 ppm of any metals, less than about 10 ppm of any metals, less than about 5 ppm of any metals, less than about 4 ppm of any metals, less than about 3 ppm of any metals, less than about 2 ppm of any metals, less than about 1 ppm of any metals, less than about 0.9 ppm of any metals, less than about 0.8 ppm of any metals, less than about 0.7 ppm of any metals, less than about 0.6 ppm of any metals, less than about 0.5 ppm of any metals, less than about 0.4 ppm of any metals, less than about 0.3 ppm of any metals, less than about 0.2 ppm of any metals, less than about 0.1 ppm of any metals. less than about 0.09 ppm of any metals, less than about 0.08 ppm of any metals, less than about 0.07 ppm of any metals, less than about 0.06 ppm of any metals, less than about 0.05 ppm of any metals, less than about 0.04 ppm of any metals, less than about 0.03 ppm of any metals, less than about 0.02 ppm of any metals, or less than about 0.01 ppm of any metals.

In some embodiments, the DMT contains less than about 10 ppm of sodium methoxide, less than about 5 ppm of sodium methoxide, less than about 4 ppm of sodium methoxide, less than about 3 ppm of sodium methoxide, less than about 2 ppm of sodium methoxide, less than about 1 ppm of sodium methoxide, less than about 0.9 ppm of sodium methoxide, less than about 0.8 ppm of sodium methoxide. less than about 0.7 ppm of sodium methoxide, less than about 0.6 ppm of sodium methoxide. less than about 0.5 ppm of sodium methoxide, less than about 0.4 ppm of sodium methoxide, less than about 0.3 ppm of sodium methoxide, less than about 0.2 ppm of sodium methoxide, less than about 0.1 ppm of sodium methoxide, less than about 0.09 ppm of sodium methoxide. less than about 0.08 ppm of sodium methoxide, less than about 0.07 ppm of sodium methoxide. less than about 0.06 ppm of sodium methoxide, less than about 0.05 ppm of sodium methoxide, less than about 0.04 ppm of sodium methoxide, less than about 0.03 ppm of sodium methoxide, less than about 0.02 ppm of sodium methoxide, or less than about 0.01 ppm of sodium methoxide.

In some embodiments, the DMT is obtained in between about 50 and about 99 mol % yield. In some embodiments, the DMT is obtained in between about 60 and about 99 mol % yield. In some embodiments, the DMT is obtained in between about 70 and about 99 mol % yield. In some embodiments. the DMT is obtained in between about 80 and about 99 mol % yield. In some embodiments, the DMT is obtained in between about 85 and about 99 mol % yield. In some embodiments, the DMT is obtained in between about 90 and about 99 mol % yield. In some embodiments, the DMT is obtained in at least about 50 mol % yield. In some embodiments, the DMT is obtained in at least about 55 mol % yield. In some embodiments, the DMT is obtained in at least about 60 mol % yield. In some embodiments, the DMT is obtained in at least about 65 mol % yield. In some embodiments, the DMT is obtained in at least about 70 mol % yield. In some embodiments, the DMT is obtained in at least about 75 mol % yield. In some embodiments, the DMT is obtained in at least about 80 mol % yield. In some embodiments, the DMT is obtained in at least about 85 mol % yield. In some embodiment, the DMT is obtained in at least about 90 mol % yield. In some embodiments, the DMT is obtained in at least about 95 mol % yield. In some embodiments, the DMT is obtained in at least about 99 mol % yield.

MEG

Described herein is a process for the depolymerization of polyethylene terephthalate (PET) comprised in a feedstock to form dimethyl terephthalate (DMT) and mono ethylene glycol (MEG).

In some embodiments, the MEG contains less than about 10% impurity (w/w). In some embodiments, the MEG contains less than about 9% impurity (w/w). In some embodiments, the MEG contains less than about 8% impurity (w/w). In some embodiments, the MEG contains less than about 7% impurity (w/w). In some embodiments, the MEG contains less than 6% impurity (w/w). In some embodiments, the MEG contains less than about 5% impurity (w/w). In some embodiments, the MEG contains less than about 4% impurity (w/w). In some embodiments, the MEG contains less than about 3% impurity (w/w). In some embodiments, the MEG contains less than about 2% impurity (w/w). In some embodiments, the MEG contains less than about 1% impurity (w/w). In some embodiments, the MEG contains less than about 0.5% impurity (w/w). In some embodiments, the MEG contains less than about 0.4% impurity (w/w). In some embodiments, the MEG contains less than about 0.3% impurity (w/w). In some embodiments, the MEG contains less than about 0.2% impurity (w/w). In some embodiments, the MEG contains less than about 0.1% impurity (w/w).

In some embodiments, the MEG is obtained in between about 50 and about 99 mol % yield. In some embodiments, the MEG is obtained in between about 60 and about 99 mol % yield. In some embodiments, the MEG is obtained in between about 70 and about 99 mol % yield. In some embodiments, the MEG is obtained in between about 80 and about 99 mol % yield. In some embodiments, the MEG is obtained in between about 85 and about 99 mol % yield. In some embodiments, the MEG is obtained in between about 90 and about 99 mol % yield. In some embodiments, the MEG is obtained in at least about 50 mol % yield. In some embodiments, the MEG is obtained in at least about 55 mol % yield. In some embodiments, the MEG is obtained in at least about 60 mol % yield. In some embodiments, the MEG is obtained in at least about 65 mol % yield. In some embodiments, the MEG is obtained in at least about 70 mol % yield. In some embodiments, the MEG is obtained in at least about 75 mol % yield. In some embodiments, the MEG is obtained in at least about 80 mol % yield. In some embodiments, the MEG is obtained in at least about 85 mol % yield. In some embodiments, the MEG is obtained in at least about 90 mol % yield. In some embodiments, the MEG is obtained in at least about 95 mol % yield. In some embodiments, the MEG is obtained in at least about 99 mol % yield.

Sodium Methoxide

Described herein is a process for the depolymerization of polyethylene terephthalate (PET) comprised in a feedstock to form dimethyl terephthalate (DMT) and mono ethylene glycol (MEG).

In some embodiments, the process described herein comprises a catalytic amount of sodium methoxide. In some embodiments, the process described herein comprises a sub-stoichiometric amount of sodium methoxide.

"Sub-stoichiometric amount", as used herein. is used to indicate that the amount of material used is less than a stoichiometric amount. The term is used herein interchangeably with "catalytic amount." In some embodiments, a sub-stoichiometric amount is less than or equal to about 95% of a stoichiometric amount. In some embodiments, a sub-stoichiometric amount is less than or equal to about 90% of a stoichiometric amount. In some embodiments, a sub-stoichiometric amount is less than or equal to about 85% of a stoichiometric amount. In some embodiments, a sub-stoichiometric amount is less than or equal to about 80% of a stoichiometric amount. In some embodiments, a sub-stoichiometric amount is less than or equal to about 75% of a stoichiometric amount. In some embodiments, a sub-stoichiometric amount is less than or equal to about 70% of a stoichiometric amount. In some embodiments, a sub-stoichiometric amount is less than or equal to about 65% of a stoichiometric amount. In some embodiments, a sub-stoichiometric amount is less than or equal to about 60% of a stoichiometric amount. In some embodiments, a sub-stoichiometric amount is less than or equal to about 55% of a stoichiometric amount. In some embodiments, a sub-stoichiometric amount is less than or equal to about 50% of a stoichiometric amount. In some embodiments, a sub-stoichiometric amount is less than or equal to about 45% of a stoichiometric amount. In some embodiments, a sub-stoichiometric amount is less than or equal to about 40% of a stoichiometric amount. In some embodiments, a sub-stoichiometric amount is less than or equal to about 35% of a stoichiometric amount. In some embodiments, a sub-stoichiometric amount is less than or equal to about 30% of a stoichiometric amount. In some embodiments, a sub-stoichiometric amount is less than or equal to about 25% of a stoichiometric amount. In some embodiments, a sub-stoichiometric amount is less than or equal to about 20% of a stoichiometric amount. In some embodiments, a sub-stoichiometric amount is less than or equal to about 15% of a stoichiometric amount. In some embodiments, a sub-stoichiometric amount is less than or equal to about 10% of a stoichiometric amount.

"Stoichiometric amount", as used herein, is used to indicate that the amount of material used is equivalent to the number of ester linkages present in the polyester.

In some embodiments of a process for the depolymerization of polyethylene terephthalate (PET), the ratio of sodium methoxide to polyethylene terephthalate (PET) is between about 1:2 and about 1:28 (mol/mol). In some embodiments of a process for the depolymerization of polyethylene terephthalate (PET), the ratio of sodium methoxide to polyethylene terephthalate (PET) is between about 1:5 and about 1:20 (mol/mol). In some embodiments of a process for the depolymerization of polyethylene terephthalate (PET), the ratio of sodium methoxide to polyethylene terephthalate (PET) is between about 1:10 and about 1:20 (mol/mol). In some embodiments of a process for the depolymerization of polyethylene terephthalate (PET), the ratio of sodium methoxide to polyethylene terephthalate (PET) is between about 1:10 and about 1:15 (mol/mol).

Depolymerization Process

Described herein is a process for the depolymerization of polyethylene terephthalate (PET) comprised in a feedstock to form dimethyl terephthalate (DMT) and mono ethylene glycol (MEG); the process comprising:
(i) mixing the feedstock comprising polyethylene terephthalate (PET) with a first portion of methanol to form a first mixture;
(ii) adding sodium methoxide to the first mixture:
(iii) admixing; and
(iv) adding a second portion of methanol thereby forming a second mixture;
thereby forming dimethyl terephthalate (DMT) and mono ethylene glycol (MEG).
Step (i)
In some embodiments, the process described herein comprises pre-treating the polyethylene terephthalate (PET) with a first portion of methanol solvent for swelling the polyethylene terephthalate (PET) prior to the addition of the sodium methoxide.

In some embodiments of a process for the depolymerization of polyethylene terephthalate (PET), the amount of the first portion of methanol is between about 0.1 and about 0.5 kg/kg of feedstock. In some embodiments of a process for the depolymerization of polyethylene terephthalate (PET), the amount of the first portion of methanol is between about 0.2 and about 0.4 kg/kg of feedstock. In some embodiments of a process for the depolymerization of polyethylene terephthalate (PET), the amount of the first portion of methanol is between about 0.1 and about 0.3 kg/kg of feedstock. In some embodiments of a process for the depolymerization of polyethylene terephthalate (PET), the amount of the first portion of methanol is between about 0.3 and about 0.5 kg/kg of feedstock. In some embodiments of a process for the depolymerization of polyethylene terephthalate (PET), the amount of the first portion of methanol is about 0.1 kg/kg of feedstock. In some embodiments of a process for the depolymerization of polyethylene terephthalate (PET), the amount of the first portion of methanol is about 0.2 kg/kg of feedstock. In some embodiments of a process for the depolymerization of polyethylene terephthalate (PET), the amount of the first portion of methanol is about 0.3 kg/kg of feedstock. In some embodiments of a process for the depolymerization of polyethylene terephthalate (PET), the amount of the first portion of methanol is about 0.4 kg/kg of feedstock. In some embodiments of a process for the depolymerization of polyethylene terephthalate (PET), the amount of the first portion of methanol is about 0.5 kg/kg of feedstock.

In some embodiments of a process for the depolymerization of polyethylene terephthalate (PET), step (i) is conducted for about 15 mins to about 120 mins. In some embodiments of a process for the depolymerization of polyethylene terephthalate (PET), step (i) is conducted for about 15 mins to about 90 mins. In some embodiments of a process for the depolymerization of polyethylene terephthalate (PET), step (i) is conducted for about 15 mins to about 60 mins. In some embodiments of a process for the depolymerization of polyethylene terephthalate (PET), step (i) is conducted for about 30 mins to about 120 mins. In some embodiments of a process for the depolymerization of polyethylene terephthalate (PET), step (i) is conducted for about 60 mins to about 120 mins. In some embodiments of a process for the depolymerization of polyethylene terephthalate (PET), step (i) is conducted for about 45 mins to about 90 mins. In some embodiments of a process for the depolymerization of polyethylene terephthalate (PET), step (i) is conducted for about 45 mins to about 60 mins. In some embodiments of a process for the depolymerization of polyethylene terephthalate (PET), step (i) is conducted for about 60 mins to about 90 mins. In some embodiments of a process for the depolymerization of polyethylene terephthalate (PET), step (i) is conducted for about 15 min. In some embodiments of a process for the depolymerization of polyethylene terephthalate (PET), step (i) is conducted for about 20 min. In some embodiments of a process for the depolymerization of polyethylene terephthalate (PET), step (i) is conducted for about 25 min. In some embodiments of a process for the depolymerization of polyethylene terephthalate (PET), step (i) is conducted for about 30 min. In some embodiments of a process for the depolymerization of polyethylene terephthalate (PET), step (i) is conducted for about 35 min. In some embodiments of a process for the depolymerization of polyethylene terephthalate (PET), step (i) is conducted for about 40 min. In some embodiments of a process for the depolymerization of polyethylene terephthalate (PET), step (i) is conducted for about 45 min. In some embodiments of a process for the depolymerization of polyethylene terephthalate (PET), step (i) is conducted for about 50 min. In some embodiments of a process for the depolymerization of polyethylene terephthalate (PET), step (i) is conducted for about 55 min. In some embodiments of a process for the depolymerization of polyethylene terephthalate (PET), step (i) is conducted for about 60 min. In some embodiments of a process for the depolymerization of polyethylene terephthalate (PET), step (i) is conducted for about 65 min. In some embodiments of a process for the depolymerization of polyethylene terephthalate (PET), step (i) is conducted for about 70 min. In some embodiments of a process for the depolymerization of polyethylene terephthalate (PET), step (i) is conducted for about 75 min. In some embodiments of a process for the depolymerization of polyethylene terephthalate (PET), step (i) is conducted for about 80 min. In some embodiments of a process for the depolymerization of polyethylene terephthalate (PET), step (i) is conducted for about 85 min. In some embodiments of a process for the depolymerization of polyethylene terephthalate (PET), step (i) is conducted for about 90 min. In some embodiments of a process for the depolymerization of polyethylene terephthalate (PET), step (i) is conducted for about 95 min. In some embodiments of a process for the depolymerization of polyethylene terephthalate (PET), step (i) is conducted for about 100 min. In some embodiments of a process for the depolymerization of polyethylene terephthalate (PET), step (i) is conducted for about 105 min. In some embodiments of a process for the depolymerization of polyethylene terephthalate (PET), step (i) is conducted for about 110 min. In some embodiments of a process for the depolymerization of polyethylene terephthalate (PET), step (i) is conducted for about 115 min. In some embodiments of a process for the depolymerization of polyethylene terephthalate (PET). step (i) is conducted for about 120 min.

In some embodiments of a process for the depolymerization of polyethylene terephthalate (PET). step (i) is conducted at a temperature between about 25° C. to about 100° C. In some embodiments of a process for the depolymerization of polyethylene terephthalate (PET), step (i) is conducted at a temperature between about 25° C. to about 60° C. In some embodiments of a process for the depolymerization of polyethylene terephthalate (PET), step (i) is conducted at a temperature between about 25° C. to about 80° C. In some embodiments of a process for the depolymerization of polyethylene terephthalate (PET), step (i) is conducted at a temperature between about 50° C. to about 100° C. In some embodiments of a process for the depolymerization of polyethylene terephthalate (PET), step (i) is conducted at a temperature between about 60° C. to about 90° C. In some embodiments of a process for the depolymerization of polyethylene terephthalate (PET), step (i) is conducted at a temperature of about 25° C. In some embodiments of a process for the depolymerization of polyethylene terephthalate (PET), step (i) is conducted at a temperature of about 30° C. In some embodiments of a process for the depolymerization of polyethylene terephthalate (PET), step (i) is conducted at a temperature of about 35° C. In some embodiments of a process for the depolymerization of polyethylene terephthalate (PET), step (i) is conducted at a temperature of about 40° C. In some embodiments of a process for the depolymerization of polyethylene terephthalate (PET), step (i) is conducted at a temperature of about 45° C. In some embodiments of a process for the depolymerization of polyethylene terephthalate (PET), step (i) is conducted at a temperature of about 50° C. In some embodiments of a process for the depolymerization of polyethylene terephthalate (PET), step (i) is conducted at a temperature of about 55° C. In some embodiments of a process for the depolymerization of polyethylene terephthalate (PET), step (i) is conducted at a temperature of about 60° C. In some embodiments of a process for the depolymerization of polyethylene terephthalate (PET), step (i) is conducted at a temperature of about 65° C. In some embodiments of a process for the depolymerization of polyethylene terephthalate (PET), step (i) is conducted at a temperature of about 70° C. In some embodiments of a process for the depolymerization of polyethylene terephthalate (PET), step (i) is conducted at a temperature of about 75° C. In some embodiments of a process for the depolymerization of polyethylene terephthalate (PET), step (i) is conducted at a temperature of about 80° C. In some embodiments of a process for the depolymerization of polyethylene terephthalate (PET), step (i) is conducted at a temperature of about 85° C. In some embodiments of a process for the depolymerization of polyethylene terephthalate (PET), step (i) is conducted at a temperature of about 90° C. In some embodiments of a process for the depolymerization of polyethylene terephthalate (PET). step (i) is conducted at a temperature of about 95° C. In some embodiments of a process for the depolymerization of polyethylene terephthalate (PET), step (i) is conducted at a temperature of about 100° C.

Step (iii)

In some embodiments of a process for the depolymerization of polyethylene terephthalate (PET), step (iii) is conducted for about 10 min to about 120 min. In some embodiments of a process for the depolymerization of polyethylene terephthalate (PET), step (iii) is conducted for about 10 min to about 90 min. In some embodiments of a process for the depolymerization of polyethylene terephthalate (PET), step (iii) is conducted for about 10 min to about 60 min. In some embodiments of a process for the depolymerization of polyethylene terephthalate (PET), step (iii) is conducted for about 10 min to about 45 min. In some embodiments of a process for the depolymerization of polyethylene terephthalate (PET), step (iii) is conducted for about 10 min to about 30 min. In some embodiments of a process for the depolymerization of polyethylene terephthalate (PET), step (iii) is conducted for about 30 min to about 120 min. In some embodiments of a process for the depolymerization of polyethylene terephthalate (PET), step (iii) is conducted for about 60 min to about 120 min. In some embodiments of a process for the depolymerization of polyethylene terephthalate (PET), step (iii) is conducted for about 90 min to about 120 min. In some embodiments of a process for the depolymerization of polyethylene terephthalate (PET), step (iii) is conducted for about 10 min. In some embodiments of a process for the depolymerization of polyethylene terephthalate (PET), step (iii) is conducted for about 15 min. In some embodiments of a process for the depolymerization of polyethylene terephthalate (PET), step (iii) is conducted for about 20 min. In some embodiments of a process for the depolymerization of polyethylene terephthalate (PET), step (iii) is conducted for about 25 min. In some embodiments of a process for the depolymerization of polyethylene terephthalate (PET), step (iii) is conducted for about 30 min. In some embodiments of a process for the depolymerization of polyethylene terephthalate (PET), step (iii) is conducted for about 35 min. In some embodiments of a process for the depolymerization of polyethylene terephthalate (PET), step (iii) is conducted for about 40 min. In some embodiments of a process for the depolymerization of polyethylene terephthalate (PET), step (iii) is conducted for about 45 min. In some embodiments of a process for the depolymerization of polyethylene terephthalate (PET), step (iii) is conducted for about 50 min. In some embodiments of a process for the depolymerization of polyethylene terephthalate (PET), step (iii) is conducted for about 55 min. In some embodiments of a process for the depolymerization of polyethylene terephthalate (PET), step (iii) is conducted for about 60 min. In some embodiments of a process for the depolymerization of polyethylene terephthalate (PET), step (iii) is conducted for about 65 min. In some embodiments of a process for the depolymerization of polyethylene terephthalate (PET), step (iii) is conducted for about 70 min. In some embodiments of a process for the depolymerization of polyethylene terephthalate (PET), step (iii) is conducted for about 75 min. In some embodiments of a process for the depolymerization of polyethylene terephthalate (PET), step (iii) is conducted for about 80 min. In some embodiments of a process for the depolymerization of polyethylene terephthalate (PET), step (iii) is conducted for about 85 min. In some embodiments of a process for the depolymerization of polyethylene terephthalate (PET), step (iii) is conducted for about 90 min. In some embodiments of a process for the depolymerization of polyethylene terephthalate (PET), step (iii) is conducted for about 95 min. In some embodiments of a process for the depolymerization of polyethylene terephthalate (PET), step (iii) is conducted for about 100 min. In some embodiments of a process for the depolymerization of polyethylene terephthalate (PET), step (iii) is conducted for about 105 min. In some embodiments of a process for the depolymerization of polyethylene terephthalate (PET), step (iii) is conducted for about 110 min. In some embodiments of a process for the depolymerization of polyethylene terephthalate (PET), step (iii) is conducted for about 115 min. In some embodiments of a process for the depolymerization of polyethylene terephthalate (PET), step (iii) is conducted for about 120 min.

In some embodiments of a process for the depolymerization of polyethylene terephthalate (PET), step (iii) is conducted at a temperature between about 40° C. to about 100° C. In some embodiments of a process for the depolymerization of polyethylene terephthalate (PET), step (iii) is conducted at a temperature between about 50° C. to about 100° C. In some embodiments of a process for the depolymerization of polyethylene terephthalate (PET), step (iii) is conducted at a temperature between about 60° C. to about 100° C. In some embodiments of a process for the depolymerization of polyethylene terephthalate (PET), step (iii) is conducted at a temperature between about 70° C. to about 100° C. In some embodiments of a process for the depolymerization of polyethylene terephthalate (PET), step (iii) is conducted at a temperature between about 80° C. to about 100° C. In some embodiments of a process for the depolymerization of polyethylene terephthalate (PET), step (iii) is conducted at a temperature of between about 85° C. to about 90° C. In some embodiments of a process for the depolymerization of polyethylene terephthalate (PET), step (iii) is conducted at a temperature of about 40° C. In some embodiments of a process for the depolymerization of polyethylene terephthalate (PET), step (iii) is conducted at a temperature of about 45° C. In some embodiments of a process for the depolymerization of polyethylene terephthalate (PET), step (iii) is conducted at a temperature of about 50° C. In some embodiments of a process for the depolymerization of polyethylene terephthalate (PET), step (iii) is conducted at a temperature of about 55° C. In some embodiments of a process for the depolymerization of polyethylene terephthalate (PET), step (iii) is conducted at a temperature of about 60° C. In some embodiments of a process for the depolymerization of polyethylene terephthalate (PET), step (iii) is conducted at a temperature of about 65° C. In some embodiments of a process for the depolymerization of polyethylene terephthalate (PET), step (iii) is conducted at a temperature of about 70° C. In some embodiments of a process for the depolymerization of polyethylene terephthalate (PET). step (iii) is conducted at a temperature of about 75° C. In some embodiments of a process for the depolymerization of polyethylene terephthalate (PET), step (iii) is conducted at a temperature of about 80° C. In some embodiments of a process for the depolymerization of polyethylene terephthalate (PET), step (iii) is conducted at a temperature of about 85° C. In some embodiments of a process for the depolymerization of polyethylene terephthalate (PET), step (iii) is conducted at a temperature of about 90° C. In some embodiments of a process for the depolymerization of polyethylene terephthalate (PET), step (iii) is conducted at a temperature of about 95° C. In some embodiments of a process for the depolymerization of polyethylene terephthalate (PET), step (iii) is conducted at a temperature of about 100° C.

Step (iv)

In some embodiments of a process for the depolymerization of polyethylene terephthalate (PET), methanol in consumed during the depolymerization process to form dimethyl terephthalate (DMT). In some embodiments of a process for the depolymerization of polyethylene terephthalate (PET), a second portion of methanol is added.

In some embodiments of a process for the depolymerization of polyethylene terephthalate (PET), the second portion of methanol is provided to maintain the sodium methoxide concentration in the second mixture between about 0.2 wt-% and about 5.0 wt-%. In some embodiments of a process for the depolymerization of polyethylene terephthalate (PET), the second portion of methanol is provided to maintain the sodium methoxide concentration in the second mixture between about 0.2 wt-% and about 4.0 wt-%. In some embodiments of a process for the depolymerization of polyethylene terephthalate (PET), the second portion of methanol is provided to maintain the sodium methoxide concentration in the second mixture between about 0.2 wt-% and about 3.0 wt-%. In some embodiments of a process for the depolymerization of polyethylene terephthalate (PET). the second portion of methanol is provided to maintain the sodium methoxide concentration in the second mixture between about 0.2 wt-% and about 2.0 wt-%. In some embodiments of a process for the depolymerization of polyethylene terephthalate (PET). the second portion of methanol is provided to maintain the sodium methoxide concentration in the second mixture between about 0.2 wt-% and about 1.5 wt-%. In some embodiments of a process for the depolymerization of polyethylene terephthalate (PET), the second portion of methanol is provided to maintain the sodium methoxide concentration in the second mixture between about 0.5 wt-% and about 1.0 wt-%. In some embodiments of a process for the depolymerization of polyethylene terephthalate (PET), the second portion of methanol is provided to maintain the sodium methoxide concentration in the second mixture at about 0.7 wt-%. In some embodiments of a process for the depolymerization of polyethylene terephthalate (PET). the second portion of methanol is provided to maintain the sodium methoxide concentration in the second mixture at about 0.2 wt-%, about 0.3 wt-%. about 0.4 wt-%. about 0.5 wt-%. about 0.6 wt-%. about 0.7 wt-%, about 0.8 wt-%. about 0.9 wt-%. about 1 wt-%. about 1.1 wt-%. about 1.2 wt-%. about 1.3 wt-%. about 1.4 wt-%, about 1.5 wt-%, about 1.6 wt-%. about 1.7 wt-%. about 1.8 wt-%. about 1.9 wt-%. about 2 wt-%. about 2.1 wt-%, about 2.2 wt-%, about 2.3 wt-%, about 2.4 wt-%, about 2.5 wt-%. about 2.6 wt-%. about 2.7 wt-%. about 2.8 wt-%, about 2.9 wt-%, about 3 wt-%. about 3.1 wt-%. about 3.2 wt-%. about 3.3 wt-%. about 3.4 wt-%, about 3.5 wt-%. about 3.6 wt-%. about 3.7 wt-%. about 3.8 wt-%. about 3.9 wt-%. about 4 wt-%. about 4.1 wt-%, about 4.2 wt-%. about 4.3 wt-%. about 4.4 wt-%. about 4.5 wt-%, about 4.6 wt-%, about 4.7 wt-%. about 4.8 wt-%, about 4.9 wt-%. or about 5 wt-%.

In some embodiments of a process for the depolymerization of polyethylene terephthalate (PET), step (iv) is conducted at a temperature between about 25° C. to about 100° C. In some embodiments of a process for the depolymerization of polyethylene terephthalate (PET), step (iv) is conducted at a temperature between about 25° C. to about 60° C. In some embodiments of a process for the depolymerization of polyethylene terephthalate (PET), step (iv) is conducted at a temperature between about 25° C. to about 80° C. In some embodiments of a process for the depolymerization of polyethylene terephthalate (PET), step (iv) is conducted at a temperature between about 50° C. to about 100° C. In some embodiments of a process for the depolymerization of polyethylene terephthalate (PET). step (iv) is conducted at a temperature between about 60° C. to about 90° C. In some embodiments of a process for the depolymerization of polyethylene terephthalate (PET), step (iv) is conducted at a temperature of about 25° C. In some embodiments of a process for the depolymerization of polyethylene terephthalate (PET), step (iv) is conducted at a temperature of about 30° C. In some embodiments of a process for the depolymerization of polyethylene terephthalate (PET), step (iv) is conducted at a temperature of about 35° C. In some embodiments of a process for the depolymerization of polyethylene terephthalate (PET), step (iv) is conducted at a temperature of about 40° C. In some embodiments of a process for the depolymerization of polyethylene terephthalate (PET), step (iv) is conducted at a temperature of about 45° C. In some embodiments of a process for the depolymerization of polyethylene terephthalate (PET), step (iv) is conducted at a temperature of about 50° C. In some embodiments of a process for the depolymerization of polyethylene terephthalate (PET), step (iv) is conducted at a temperature of about 55° C. In some embodiments of a process for the depolymerization of polyethylene terephthalate (PET), step (iv) is conducted at a temperature of about 60° C. In some embodiments of a process for the depolymerization of polyethylene terephthalate (PET), step (iv) is conducted at a temperature of about 65° C. In some embodiments of a process for the depolymerization of polyethylene terephthalate (PET), step (iv) is conducted at a temperature of about 70° C. In some embodiments of a process for the depolymerization of polyethylene terephthalate (PET), step (iv) is conducted at a temperature of about 75° C. In some embodiments of a process for the depolymerization of polyethylene terephthalate (PET), step (iv) is conducted at a temperature of about 80° C. In some embodiments of a process for the depolymerization of polyethylene terephthalate (PET), step (iv) is conducted at a temperature of about 85° C. In some embodiments of a process for the depolymerization of polyethylene terephthalate (PET), step (iv) is conducted at a temperature of about 90° C. In some embodiments of a process for the depolymerization of polyethylene terephthalate (PET), step (iv) is conducted at a temperature of about 95° C. In some embodiments of a process for the depolymerization of polyethylene terephthalate (PET), step (iv) is conducted at a temperature of about 100° C.

In some embodiments of a process for the depolymerization of polyethylene terephthalate (PET), step (iv) is conducted for a total time between about 1 hour and about 10 hours. In some embodiments of a process for the depolymerization of polyethylene terephthalate (PET), step (iv) is conducted for a total time between about 1 hour and about 8 hours. In some embodiments of a process for the depolymerization of polyethylene terephthalate (PET), step (iv) is conducted for a total time between about 1 hour and about 5 hours. In some embodiments of a process for the depolymerization of polyethylene terephthalate (PET), step (iv) is conducted for a total time between about 4 hour and about 6 hours. In some embodiments of a process for the depolymerization of polyethylene terephthalate (PET), step (iv) is conducted for a total time between about 3 hour and about 7 hours.

Sequential Addition

In some embodiments of a process for the depolymerization of polyethylene terephthalate (PET), the second portion of methanol is provided sequentially at predetermined times in step (iv). In some embodiments of a process for the depolymerization of polyethylene terephthalate (PET), the second portion of methanol is provided in fractions at predetermined times in step (iv). In some embodiments of a process for the depolymerization of polyethylene terephthalate (PET), the second portion of methanol is provided in one, two, three, four, five, six, seven, eight, nine, or ten fractions. In some embodiments of a process for the depolymerization of polyethylene terephthalate (PET), the second portion of methanol is provided in one, two, three, four, or five fractions. In some embodiments of a process for the depolymerization of polyethylene terephthalate (PET), the second portion of methanol is provided in one, two, or three fractions. In some embodiments of a process for the depolymerization of polyethylene terephthalate (PET), the second portion of methanol is provided in two or three fractions. In some embodiments of a process for the depolymerization of polyethylene terephthalate (PET), the second portion of methanol is provided in two fractions. In some embodiments of a process for the depolymerization of polyethylene terephthalate (PET), the second portion of methanol is provided in three fractions. In some embodiments of a process for the depolymerization of polyethylene terephthalate (PET). the second portion of methanol is provided in four fractions. In some embodiments of a process for the depolymerization of polyethylene terephthalate (PET), the second portion of methanol is provided in five fractions. In some embodiments of a process for the depolymerization of polyethylene terephthalate (PET), the second portion of methanol is provided in six fractions. In some embodiments of a process for the depolymerization of polyethylene terephthalate (PET), the second portion of methanol is provided in seven fractions. In some embodiments of a process for the depolymerization of polyethylene terephthalate (PET), the second portion of methanol is provided in eight fractions. In some embodiments of a process for the depolymerization of polyethylene terephthalate (PET), the second portion of methanol is provided in nine fractions. In some embodiments of a process for the depolymerization of polyethylene terephthalate (PET), the second portion of methanol is provided in ten fractions.

In some embodiments of a process for the depolymerization of polyethylene terephthalate (PET), the mixture is admixed in between each fraction addition.

In some embodiments of a process for the depolymerization of polyethylene terephthalate (PET), a first fraction of the second portion of methanol is provided about 1 min to about 60 min after the addition of sodium methoxide. In some embodiments of a process for the depolymerization of polyethylene terephthalate (PET), a first fraction of the second portion of methanol is provided about 15 min to about 45 min after the addition of sodium methoxide. In some embodiments of a process for the depolymerization of polyethylene terephthalate (PET), a first fraction of the second portion of methanol is provided about 1 min after the addition of sodium methoxide. In some embodiments of a process for the depolymerization of polyethylene terephthalate (PET), a first fraction of the second portion of methanol is provided about 5 min after the addition of sodium methoxide. In some embodiments of a process for the depolymerization of polyethylene terephthalate (PET), a first fraction of the second portion of methanol is provided about 10 min after the addition of sodium methoxide. In some embodiments of a process for the depolymerization of polyethylene terephthalate (PET), a first fraction of the second portion of methanol is provided about 15 min after the addition of sodium methoxide. In some embodiments of a process for the depolymerization of polyethylene terephthalate (PET), a first fraction of the second portion of methanol is provided about 20 min after the addition of sodium methoxide. In some embodiments of a process for the depolymerization of polyethylene terephthalate (PET), a first fraction of the second portion of methanol is provided about 25 min after the addition of sodium methoxide. In some embodiments of a process for the depolymerization of polyethylene terephthalate (PET), a first fraction of the second portion of methanol is provided about 30 min after the addition of sodium methoxide. In some embodiments of a process for the depolymerization of polyethylene terephthalate (PET), a first fraction of the second portion of methanol is provided about 35 min after the addition of sodium methoxide. In some embodiments of a process for the depolymerization of polyethylene terephthalate (PET), a first fraction of the second portion of methanol is provided about 40 min after the addition of sodium methoxide. In some embodiments of a process for the depolymerization of polyethylene terephthalate (PET), a first fraction of the second portion of methanol is provided about 45 min after the addition of sodium methoxide. In some embodiments of a process for the depolymerization of polyethylene terephthalate (PET), a first fraction of the second portion of methanol is provided about 50 min after the addition of sodium methoxide. In some embodiments of a process for the depolymerization of polyethylene terephthalate (PET), a first fraction of the second portion of methanol is provided about 55 min after the addition of sodium methoxide. In some embodiments of a process for the depolymerization of polyethylene terephthalate (PET), a first fraction of the second portion of methanol is provided about 60 min after the addition of sodium methoxide.

In some embodiments of a process for the depolymerization of polyethylene terephthalate (PET), the amount of the first fraction of the second portion of methanol is between about 10 g/kg of feedstock and about 100 g/kg of feedstock. In some embodiments of a process for the depolymerization of polyethylene terephthalate (PET), the amount of the first fraction of the second portion of methanol is between about 50 g/kg of feedstock and about 100 g/kg of feedstock. In some embodiments of a process for the depolymerization of polyethylene terephthalate (PET), the amount of the first fraction of the second portion of methanol is between about 50 g/kg of feedstock and about 80 g/kg of feedstock. In some embodiments of a process for the depolymerization of polyethylene terephthalate (PET), the amount of the first fraction of the second portion of methanol is about 10 g/kg of feedstock. In some embodiments of a process for the depolymerization of polyethylene terephthalate (PET), the amount of the first fraction of the second portion of methanol is about 20 g/kg of feedstock. In some embodiments of a process for the depolymerization of polyethylene terephthalate (PET), the amount of the first fraction of the second portion of methanol is about 30 g/kg of feedstock. In some embodiments of a process for the depolymerization of polyethylene terephthalate (PET), the amount of the first fraction of the second portion of methanol is about 40 g/kg of feedstock. In some embodiments of a process for the depolymerization of polyethylene terephthalate (PET), the amount of the first fraction of the second portion of methanol is about 50 g/kg of feedstock. In some embodiments of a process for the depolymerization of polyethylene terephthalate (PET), the amount of the first fraction of the second portion of methanol is about 60 g/kg of feedstock. In some embodiments of a process for the depolymerization of polyethylene terephthalate (PET), the amount of the first fraction of the second portion of methanol is about 70 g/kg of feedstock. In some embodiments of a process for the depolymerization of polyethylene terephthalate (PET), the amount of the first fraction of the second portion of methanol is about 80 g/kg of feedstock. In some embodiments of a process for the depolymerization of polyethylene terephthalate (PET), the amount of the first fraction of the second portion of methanol is about 90 g/kg of feedstock. In some embodiments of a process for the depolymerization of polyethylene terephthalate (PET), the amount of the first fraction of the second portion of methanol is about 100 g/kg of feedstock.

In some embodiments of a process for the depolymerization of polyethylene terephthalate (PET), a second fraction of the second portion of methanol is provided about 30 min to about 90 min after the addition of sodium methoxide. In some embodiments of a process for the depolymerization of polyethylene terephthalate (PET), a second fraction of the second portion of methanol is provided about 45 min to about 75 min after the addition of sodium methoxide. In some embodiments of a process for the depolymerization of polyethylene terephthalate (PET), a second fraction of the second portion of methanol is provided about 30 min after the addition of sodium methoxide. In some embodiments of a process for the depolymerization of polyethylene terephthalate (PET), a second fraction of the second portion of methanol is provided about 35 min after the addition of sodium methoxide. In some embodiments of a process for the depolymerization of polyethylene terephthalate (PET), a second fraction of the second portion of methanol is provided about 40 min after the addition of sodium methoxide. In some embodiments of a process for the depolymerization of polyethylene terephthalate (PET), a second fraction of the second portion of methanol is provided about 45 min after the addition of sodium methoxide. In some embodiments of a process for the depolymerization of polyethylene terephthalate (PET), a second fraction of the second portion of methanol is provided about 50 min after the addition of sodium methoxide. In some embodiments of a process for the depolymerization of polyethylene terephthalate (PET), a second fraction of the second portion of methanol is provided about 55 min after the addition of sodium methoxide. In some embodiments of a process for the depolymerization of polyethylene terephthalate (PET), a second fraction of the second portion of methanol is provided about 60 min after the addition of sodium methoxide. In some embodiments of a process for the depolymerization of polyethylene terephthalate (PET), a second fraction of the second portion of methanol is provided about 65 min after the addition of sodium methoxide. In some embodiments of a process for the depolymerization of polyethylene terephthalate (PET), a second fraction of the second portion of methanol is provided about 70 min after the addition of sodium methoxide. In some embodiments of a process for the depolymerization of polyethylene terephthalate (PET), a second fraction of the second portion of methanol is provided about 75 min after the addition of sodium methoxide. In some embodiments of a process for the depolymerization of polyethylene terephthalate (PET), a second fraction of the second portion of methanol is provided about 80 min after the addition of sodium methoxide. In some embodiments of a process for the depolymerization of polyethylene terephthalate (PET), a second fraction of the second portion of methanol is provided about 85 min after the addition of sodium methoxide. In some embodiments of a process for the depolymerization of polyethylene terephthalate (PET), a second fraction of the second portion of methanol is provided about 90 min after the addition of sodium methoxide.

In some embodiments of a process for the depolymerization of polyethylene terephthalate (PET), the amount of the second fraction of the second portion of methanol is between about 100 g/kg of feedstock and about 200 g/kg of feedstock. In some embodiments of a process for the depolymerization of polyethylene terephthalate (PET), the amount of the second fraction of the second portion of methanol is between about 100 g/kg of feedstock and about 150 g/kg of feedstock. In some embodiments of a process for the depolymerization of polyethylene terephthalate (PET), the amount of the second fraction of the second portion of methanol is about 100 g/kg of feedstock. In some embodiments of a process for the depolymerization of polyethylene terephthalate (PET), the amount of the second fraction of the second portion of methanol is about 110 g/kg of feedstock. In some embodiments of a process for the depolymerization of polyethylene terephthalate (PET), the amount of the second fraction of the second portion of methanol is about 120 g/kg of feedstock. In some embodiments of a process for the depolymerization of polyethylene terephthalate (PET), the amount of the second fraction of the second portion of methanol is about 130 g/kg of feedstock. In some embodiments of a process for the depolymerization of polyethylene terephthalate (PET), the amount of the second fraction of the second portion of methanol is about 140 g/kg of feedstock. In some embodiments of a process for the depolymerization of polyethylene terephthalate (PET), the amount of the second fraction of the second portion of methanol is about 150 g/kg of feedstock. In some embodiments of a process for the depolymerization of polyethylene terephthalate (PET), the amount of the second fraction of the second portion of methanol is about 160 g/kg of feedstock. In some embodiments of a process for the depolymerization of polyethylene terephthalate (PET), the amount of the second fraction of the second portion of methanol is about 170 g/kg of feedstock. In some embodiments of a process for the depolymerization of polyethylene terephthalate (PET), the amount of the second fraction of the second portion of methanol is about 180 g/kg of feedstock. In some embodiments of a process for the depolymerization of polyethylene terephthalate (PET), the amount of the second fraction of the second portion of methanol is about 190 g/kg of feedstock. In some embodiments of a process for the depolymerization of polyethylene terephthalate (PET), the amount of the second fraction of the second portion of methanol is about 200 g/kg of feedstock.

In some embodiments of a process for the depolymerization of polyethylene terephthalate (PET), a third fraction of the second portion of methanol is provided about 60 min to about 120 min after the addition of sodium methoxide. In some embodiments of a process for the depolymerization of polyethylene terephthalate (PET), a third fraction of the second portion of methanol is provided about 90 min to about 120 min after the addition of sodium methoxide. In some embodiments of a process for the depolymerization of polyethylene terephthalate (PET), a third fraction of the second portion of methanol is provided about 60 min to about 90 min after the addition of sodium methoxide. In some embodiments of a process for the depolymerization of polyethylene terephthalate (PET), a third fraction of the second portion of methanol is provided about 60 min after the addition of sodium methoxide. In some embodiments of a process for the depolymerization of polyethylene terephthalate (PET), a third fraction of the second portion of methanol is provided about 65 min after the addition of sodium methoxide. In some embodiments of a process for the depolymerization of polyethylene terephthalate (PET), a third fraction of the second portion of methanol is provided about 70 min after the addition of sodium methoxide. In some embodiments of a process for the depolymerization of polyethylene terephthalate (PET), a third fraction of the second portion of methanol is provided about 75 min after the addition of sodium methoxide. In some embodiments of a process for the depolymerization of polyethylene terephthalate (PET), a third fraction of the second portion of methanol is provided about 80 min after the addition of sodium methoxide. In some embodiments of a process for the depolymerization of polyethylene terephthalate (PET), a third fraction of the second portion of methanol is provided about 85 min after the addition of sodium methoxide. In some embodiments of a process for the depolymerization of polyethylene terephthalate (PET), a third fraction of the second portion of methanol is provided about 90 min after the addition of sodium methoxide. In some embodiments of a process for the depolymerization of polyethylene terephthalate (PET), a third fraction of the second portion of methanol is provided about 95 min after the addition of sodium methoxide. In some embodiments of a process for the depolymerization of polyethylene terephthalate (PET), a third fraction of the second portion of methanol is provided about 100 min after the addition of sodium methoxide. In some embodiments of a process for the depolymerization of polyethylene terephthalate (PET), a third fraction of the second portion of methanol is provided about 105 min after the addition of sodium methoxide. In some embodiments of a process for the depolymerization of polyethylene tereph-thalate (PET), a third fraction of the second portion of methanol is provided about 110 min after the addition of sodium methoxide. In some embodiments of a process for the depolymerization of polyethylene terephthalate (PET), a third fraction of the second portion of methanol is provided about 115 min after the addition of sodium methoxide. In some embodiments of a process for the depolymerization of polyethylene terephthalate (PET), a third fraction of the second portion of methanol is provided about 120 min after the addition of sodium methoxide.

In some embodiments of a process for the depolymerization of polyethylene terephthalate (PET). the amount of the third fraction of the second portion of methanol is between about 100 g/kg of feedstock and about 200 g/kg of feedstock. In some embodiments of a process for the depolymerization of polyethylene terephthalate (PET), the amount of the third fraction of the second portion of methanol is between about 100 g/kg of feedstock and about 150 g/kg of feedstock. In some embodiments of a process for the depolymerization of polyethylene terephthalate (PET), the amount of the third fraction of the second portion of methanol is about 100 g/kg of feedstock. In some embodiments of a process for the depolymerization of polyethylene terephthalate (PET), the amount of the third fraction of the second portion of methanol is about 110 g/kg of feedstock. In some embodiments of a process for the depolymerization of polyethylene terephthalate (PET), the amount of the third fraction of the second portion of methanol is about 120 g/kg of feedstock. In some embodiments of a process for the depolymerization of polyethylene terephthalate (PET), the amount of the third fraction of the second portion of methanol is about 130 g/kg of feedstock. In some embodiments of a process for the depolymerization of polyethylene terephthalate (PET), the amount of the third fraction of the second portion of methanol is about 140 g/kg of feedstock. In some embodiments of a process for the depolymerization of polyethylene terephthalate (PET), the amount of the third fraction of the second portion of methanol is about 150 g/kg of feedstock. In some embodiments of a process for the depolymerization of polyethylene terephthalate (PET), the amount of the third fraction of the second portion of methanol is about 160 g/kg of feedstock. In some embodiments of a process for the depolymerization of polyethylene terephthalate (PET), the amount of the third fraction of the second portion of methanol is about 170 g/kg of feedstock. In some embodiments of a process for the depolymerization of polyethylene terephthalate (PET), the amount of the third fraction of the second portion of methanol is about 180 g/kg of feedstock. In some embodiments of a process for the depolymerization of polyethylene terephthalate (PET), the amount of the third fraction of the second portion of methanol is about 190 g/kg of feedstock. In some embodiments of a process for the depolymerization of polyethylene terephthalate (PET), the amount of the third fraction of the second portion of methanol is about 200 g/kg of feedstock.

Continuous Addition

In some embodiments of a process for the depolymerization of polyethylene terephthalate (PET), the second portion of methanol is provided continuously in step (iv).

In some embodiments of a process for the depolymerization of polyethylene terephthalate (PET), the second portion of methanol is provided continuously at a rate between about 50 g/h/kg of feedstock and about 100 g/h/kg of feedstock. In some embodiments of a process for the depolymerization of polyethylene terephthalate (PET), the second portion of methanol is provided continuously at a rate between about 50 g/h/kg of feedstock and about 90 g/h/kg of feedstock. In some embodiments of a process for the depolymerization of polyethylene terephthalate (PET), the second portion of methanol is provided continuously at a rate between about 50 g/h/kg of feedstock and about 80 g/h/kg of feedstock. In some embodiments of a process for the depolymerization of polyethylene terephthalate (PET), the second portion of methanol is provided continuously at a rate between about 50 g/h/kg of feedstock and about 70 g/h/kg of feedstock. In some embodiments of a process for the depolymerization of polyethylene terephthalate (PET), the second portion of methanol is provided continuously at a rate of about 50 g/h/kg of feedstock. In some embodiments of a process for the depolymerization of polyethylene terephthalate (PET), the second portion of methanol is provided continuously at a rate of about 60 g/h/kg of feedstock. In some embodiments of a process for the depolymerization of polyethylene terephthalate (PET). the second portion of methanol is provided continuously at a rate of about 70 g/h/kg of feedstock. In some embodiments of a process for the depolymerization of polyethylene terephthalate (PET), the second portion of methanol is provided continuously at a rate of about 80 g/h/kg of feedstock. In some embodiments of a process for the depolymerization of polyethylene terephthalate (PET), the second portion of methanol is provided continuously at a rate of about 90 g/h/kg of feedstock. In some embodiments of a process for the depolymerization of polyethylene terephthalate (PET), the second portion of methanol is provided continuously at a rate of about 100 g/h/kg of feedstock.

Certain Terminology

The section headings used herein are for organizational purposes only and are not to be construed as limiting the subject matter described.

Unless defined otherwise, all technical and scientific terms used herein have the same meaning as is commonly understood to which the claimed subject matter belongs. In the event that there is a plurality of definitions for terms herein, those in this section prevail.

It is to be understood that the general description and the detailed description are exemplary and explanatory only and are not restrictive of any subject matter claimed. In this application, the use of the singular includes the plural unless specifically stated otherwise. It must be noted that, as used in the specification and the appended claims. the singular forms "a," "an" and "the" include plural referents unless the context clearly dictates otherwise. In this application, the use of "or" means "and/or" unless stated otherwise. Furthermore, use of the term "including" as well as other forms, such as "include". "includes," and "included," is not limiting.

Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

As used herein, the term "about" or "approximately" means within 10%, preferably within 10%, and more preferably within 5% of a given value or range.

As used herein, ambient temperature is a colloquial expression for the typical or preferred indoor (climate-controlled) temperature to which people are generally accustomed. It represents the small range of temperatures at which the air feels neither hot nor cold, approximately 21° C. In some embodiments. ambient temperature is 25±5° C. In some embodiments, ambient temperature is 18° C. In some embodiments, ambient temperature is 19° C. In some embodiments, ambient temperature is 20° C. In some embodiments, ambient temperature is 21° C. In some embodiments, ambient temperature is 22° C. In some embodiments, ambient temperature is 23° C. In some embodiments, ambient temperature is 24° C. In some embodiments, ambient temperature is 25° C. In some embodiments, ambient temperature is 26° C. In some embodiments, ambient temperature is 27° C. In some embodiments, ambient temperature is 28° C. In some embodiments, ambient temperature is 29° C. In some embodiments, ambient temperature is 30° C.

As used in this specification and the appended claims, depolymerization, refer to a way of breaking down a polymer to its starting material. It is essentially the opposite of polymerization. In some embodiments, the depolymerization is achieved by methanolysis.

As used herein, the term "mol" when referring to PET is the molar amount and is calculated using the molecular weight of the "PET" unit which is 192.17 g/mol.

Definition of standard chemistry terms may be found in reference works, including but not limited to, Carey and Sundberg "Advanced Organic Chemistry $4^{th}$ Ed." Vols. A (2000) and B (2001). Plenum Press, New York.

EXAMPLES

The following examples are intended to illustrate but not limit the disclosed embodiments.

Example 1: PET Depolymerization with Sequential Methanol Addition

To a 25 L reactor containing 10.00 kg of feedstock (PET fines) was added 3.00 kg of methanol. The medium was stirred and heated to 60° C. for 1 h. Then the temperature was raised to 85° C. after which sodium methoxide (30) kg/t of feedstock) was added. Fractional addition of methanol was conducted as follows: 710 g was added 30 min after the addition of sodium methoxide, 1.21 kg after another 30 min. and a final 1.21 kg after another 30 min. The reaction medium was stirred at 85° C. for a total of 8-10 h after sodium methoxide addition. Yields of reaction were: 97% for DMT and 95% for MEG.

Example 2: PET Depolymerization with Partial Methanol Removal and Sequential Methanol Addition To a 25 L reactor containing 10.00 kg of feedstock (PET fines) was added 6.00 kg of methanol. The medium was stirred and heated to 60° C. for 1 h. Then 3 kg of liquid was drained out and the temperature was raised to 85° C. after which sodium methoxide (30 kg/t of feedstock) was added. Fractional addition of methanol was conducted as follows: 1.21 kg was added 30 min after the addition of sodium methoxide, 1.21 kg after another 30 min, and a final 1.21 kg after another 30 min. The reaction medium was stirred at 85° C. for a total of 8-10 h after sodium methoxide addition. Yields of reaction were: 87% for DMT and 83% for MEG.

Example 3: PET Depolymerization with Partial Methanol Removal and Single Methanol Addition To a 25 L reactor containing 10.00 kg of feedstock (PET fines) was added 6.00 kg of methanol. The medium was stirred and heated to 60° C. for 1 h. Then 2.2 kg of liquid was drained out and the temperature raised to 85° C. after which sodium methoxide (30 kg/t of feedstock) was added. After 30 min. 2.3 kg of methanol was added. The reaction medium was stirred at 85° C. for a total of 8-10 h after sodium methoxide addition. Yields of reaction was 80% for DMT and 93% for MEG.

What is claimed is:

1. A process for depolymerizing a polyester to form a terephthalate, the processing comprising:
   (i) providing a feedstock comprising the polyester;
   ii) mixing the feedstock with a first fraction of an alcohol to form a mixture; and
   (iii) subsequent to (ii), mixing a second fraction of the alcohol and a methoxide with the mixture from (ii) to maintain a methoxide concentration in the resulting mixture while forming the terephthalate, the methoxide concentration comprising a sub-stoichiometric amount of methoxide;
   wherein the mixing in (ii) is performed at a temperature from about 50° C. to about 100° C., and wherein the mixing in (iii) is performed at a temperature from about 50° C. to about 100° C.

2. The process of claim 1, wherein the mixing in (ii) is performed at a temperature from about 70° C. to about 100° C.

3. The process of claim 1, wherein the mixing in (iii) is performed at a temperature from about 70° C. to about 100° C.

4. The process of claim 1, wherein the mixing in (ii) is performed at a temperature of about 85° C.

5. The process of claim 1, wherein the mixing in (iii) is performed at a temperature of about 85° C.

6. The process of claim 1, wherein the terephthalate is obtained in at least 70 mol % yield.

7. The process of claim 6, wherein the terephthalate is obtained in at least 80 mol % yield.

8. The process of claim 7, wherein the terephthalate is obtained in at least 90 mol % yield.

9. The process of claim 1, wherein the alcohol comprises methanol.

10. The process of claim 1, wherein the alcohol comprises ethanol.

11. The process of claim 1, wherein the methoxide comprises sodium methoxide.

12. The process of claim 1, wherein an output mixture comprising the produced terephthalate comprises less than 10 ppm of the methoxide.

13. The process of claim 1, wherein the polyester comprises polyethylene terephthalate.

14. The process of claim 1, wherein the polyester comprises polybutylene terephthalate.

15. The process of claim 1, wherein the polyester comprises polytrimethylene terephthalate.

16. The process of claim 1, wherein the feedstock comprises a contaminant.

17. The process of claim 16, wherein the contaminant comprises polyethylene.

18. The process of claim 16, wherein the contaminant comprises a polyamide.

19. The process of claim 16, wherein the contaminant comprises a colorant.

20. The process of claim 16, wherein the contaminant comprises a cellulose.

* * * * *